(12) United States Patent
Huang et al.

(10) Patent No.: US 11,312,934 B2
(45) Date of Patent: Apr. 26, 2022

(54) PIEZOELECTRIC ULTRASONIC MICROINJECTION DEVICE BASED ON FLEXIBLE HINGE MECHANISM

(71) Applicant: SOOCHOW UNIVERSITY, Suzhou (CN)

(72) Inventors: Haibo Huang, Suzhou (CN); Xiwei Gao, Suzhou (CN); Liguo Chen, Suzhou (CN); Fei Zhou, Suzhou (CN); Hao Guo, Suzhou (CN); Lingfeng Chang, Suzhou (CN); Jizhu Liu, Suzhou (CN); Yangjun Wang, Suzhou (CN); Lining Sun, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 5 days.

(21) Appl. No.: 16/958,729

(22) PCT Filed: May 22, 2018

(86) PCT No.: PCT/CN2018/087759
§ 371 (c)(1),
(2) Date: Jun. 28, 2020

(87) PCT Pub. No.: WO2019/218379
PCT Pub. Date: Nov. 21, 2019

(65) Prior Publication Data
US 2020/0332244 A1 Oct. 22, 2020

(30) Foreign Application Priority Data
May 14, 2018 (CN) .......................... 201810454388.0

(51) Int. Cl.
*C12M 1/42* (2006.01)
*B01L 3/02* (2006.01)
(Continued)

(52) U.S. Cl.
CPC ............. *C12M 35/04* (2013.01); *B01L 3/021* (2013.01); *C12M 23/16* (2013.01); *C12M 23/26* (2013.01);
(Continued)

(58) Field of Classification Search
CPC ...... C12M 35/04; C12M 23/16; C12M 23/26; C12M 23/38; B01L 3/021; B01L 2300/042; B01L 2300/123; B01L 2400/0475
See application file for complete search history.

(56) References Cited

U.S. PATENT DOCUMENTS

| 2009/0023206 A1* | 1/2009 | Nishyama .............. C12M 23/16 435/325 |
| 2009/0130743 A1 | 5/2009 | Miyawaki et al. |
| 2021/0046754 A1* | 2/2021 | Ungerer .................. B05B 1/083 |

FOREIGN PATENT DOCUMENTS

| CN | 102268360 A | 12/2011 |
| CN | 102268363 A | 12/2011 |

(Continued)

OTHER PUBLICATIONS

Machine Translation of CN104109629 (Year: 2021).*
Machine Translation of DE10 2018103049 from WIPO, downloaded Nov. 2021 (Year: 2021).*

*Primary Examiner* — William H. Beisner
*Assistant Examiner* — Danielle B Henkel
(74) *Attorney, Agent, or Firm* — SZDC Law P.C.

(57) ABSTRACT

The present invention discloses a piezoelectric ultrasonic microinjection device based on a flexible hinge mechanism. The device includes: a cover, a flexible hinge mechanism, a base, a screw cap and an end cap fixedly assembled together, the base being provided with a pump interface; and a micropipette fixedly mounted in the base, the screw cap and the end cap and extending outward, the micropipette being
(Continued)

in communication with the pump interface; wherein the flexible hinge mechanism comprises a housing, a piezoelectric ceramic package module encapsulated in the housing, a central shaft fixedly mounted with the piezoelectric ceramic package module and the base, and a vibration output shaft extending from the piezoelectric ceramic package module into the central shaft, a plurality of flexible hinge beams being disposed between the central shaft and the housing.

12 Claims, 6 Drawing Sheets

(51) Int. Cl.
    *C12M 3/06*     (2006.01)
    *C12M 1/00*     (2006.01)

(52) U.S. Cl.
    CPC ........ *C12M 23/38* (2013.01); *B01L 2300/042* (2013.01); *B01L 2300/123* (2013.01); *B01L 2400/0475* (2013.01)

(56) References Cited

FOREIGN PATENT DOCUMENTS

| | | | | |
|---|---|---|---|---|
| CN | 104109629 A | 10/2014 | | |
| DE | 102018103049 A1 * | 8/2019 | ............ | B01L 3/0268 |
| EP | 2017330 B1 | 8/2010 | | |
| WO | 2008046051 A1 | 4/2008 | | |

* cited by examiner

PIEZOELECTRIC ULTRASONIC MICROINJECTION DEVICE BASED ON FLEXIBLE HINGE MECHANISM

This application is the National Stage Application of PCT/CN2018/087759, filed on May 22, 2018, which claims priority to Chinese Patent Application No.: 201810454388.0, filed on May 14, 2018, which is incorporated by reference for all purposes as if fully set forth herein.

TECHNICAL FIELD

The present invention relates to the field of microinjection technology, in particular to a piezoelectric ultrasonic microinjection device based on a flexible hinge mechanism.

BACKGROUND

With the rapid development of biotechnology, microinjection technology has become an important means of cell engineering research such as transgenic injection, cloning technology, artificial assisted reproductive technology. Membrane rupture technology is the key technology of microinjection. When rupturing the membrane, the micropipette penetrates into the cell body, and then completes the corresponding injection tasks, such as foreign gene injection and nuclear transplantation. During the microinjection, the accuracy of the injection device directly affects the activity of the injected cells.

The piezoelectric rupture membrane injection method has been widely used in cell microinjection operations as a technique for cell micro-deformation and high injection success rate. However, the traditional piezoelectric injection device has the defects of large harmful vibration, which greatly affects the cell survival rate. In addition, the clamping device of the traditional micro-injector has poor sealing performance, and most of them adopt spiral seal or ordinary flat gasket seal. Under the ultrasonic excitation of piezoelectric ceramic, "gas leakage" and "liquid leakage" phenomenon are easy to occur, resulting in errors or pollution during experiment, which reduces the success rate of the experiment.

Therefore, in view of the above technical problems, it is necessary to provide a piezoelectric ultrasonic microinjection device based on a flexible hinge mechanism.

SUMMARY

In view of this, an object of the present invention is to provide a piezoelectric ultrasonic microinjection device based on a flexible hinge mechanism, which can effectively inhibit the harmful radial vibration of the micropipette tip during the microinjection operation, reduce the cell damage, improve injection success rate and greatly improve the sealing property of the device.

In order to achieve the above object, the technical solution provided by an embodiment of the present invention is as follows:

A piezoelectric ultrasonic microinjection device based on a flexible hinge mechanism, the device comprising:

a cover, a flexible hinge mechanism, a base, a screw cap and an end cap fixedly assembled together, the base being provided with a pump interface; and a micropipette fixedly mounted in the base, the screw cap and the end cap and extending outward, the micropipette being in communication with the pump interface;

wherein the flexible hinge mechanism comprises a housing, a piezoelectric ceramic package module encapsulated in the housing, a central shaft fixedly mounted with the piezoelectric ceramic package module and the base, and a vibration output shaft extending from the piezoelectric ceramic package module into the central shaft, a plurality of flexible hinge beams being disposed between the central shaft and the housing.

As a further improvement of the present invention, the end cap and the screw cap as well as the screw cap and the base are respectively fixedly mounted to each other through a thread.

As a further improvement of the present invention, a gasket is disposed between the end cap and the screw cap and/or between the screw cap and the base, and two sides of the gasket are different first and second tapered faces.

As a further improvement of the present invention, the end cap comprises an end cap body and an end cap mounting portion, an outer diameter of the end cap body being greater than that of the end cap mounting portion, and an outer side of the end cap mounting portion being provided with a first thread fixedly mounted to the screw cap.

As a further improvement of the present invention, a first cavity and a second cavity are formed in the end cap in a direction from the end cap body toward the end cap mounting portion, the second cavity being tapered.

As a further improvement of the present invention, the screw cap comprises a screw cap body and a screw cap mounting portion, an outer diameter of the screw cap body being greater than that of the screw cap mounting portion, an inner side of the screw cap body being provided with a second thread fixedly mounted to the end cap, and an outer side of the screw cap mounting portion being provided with a third thread fixedly mounted to the base.

As a further improvement of the present invention, a third cavity, a fourth cavity and a fifth cavity are formed in the screw cap in a direction from the screw cap body to the screw cap mounting portion, the fifth cavity being tapered.

As a further improvement of the present invention, the base comprises a bent section fixedly mounted to the screw cap, and a horizontal section fixedly mounted with the flexible hinge mechanism, the bent section and the horizontal section being respectively fixedly mounted to the screw cap and the flexible hinge mechanism through a thread.

As a further improvement of the present invention, an inner side of the bent section is provided with a fourth thread fixedly mounted to the screw cap.

As a further improvement of the present invention, a sixth cavity and a seventh cavity are provided in the bent section, and an eighth cavity is provided in the horizontal section, the seventh cavity being tapered, and the sixth cavity being in communication with the pump interface through the seventh cavity and a micro flow channel.

As a further improvement of the present invention, an inner side of the horizontal section is provided with a fifth thread, an outer side of an end of the central shaft of the flexible hinge mechanism is provided with a sixth thread, and the base and the flexible hinge mechanism are fixedly mounted through the fifth thread and the sixth thread.

As a further improvement of the present invention, an end of the horizontal section is provided with a first flange, and a plurality of first reinforcing ribs is provided between the first flange and the horizontal section.

As a further improvement of the present invention, the central shaft of the flexible hinge mechanism is provided with a second flange, and a plurality of second reinforcing ribs is provided between the second flange and the central shaft.

As a further improvement of the present invention, the flexible hinge beam is provided with a plurality of V-shaped recesses.

As a further improvement of the present invention, the flexible hinge beam is distributed in an circumferential array with an equal angle of 120 [deg.] centered on the central shaft, and the flexible hinge beam in each direction is distributed in a parallel linear array of equidistant double flexible hinge beams at a certain distance in the axial direction.

As a further improvement of the present invention, the central shaft is provided with a mounting hole, and a screw is fixedly mounted in the mounting hole to fix the central shaft and the vibration output shaft.

The beneficial effects of the present invention are as follows:

aiming at the harmful radial vibration transmitted by the piezoelectric ceramic package module to the micropipette tip, a three-dimensional flexible hinge mechanism is designed for the piezoelectric ceramic package module, which can effectively filter and buffer the radial harmful vibration of the vibration output shaft while maintaining a high energy transmission efficiency, thereby reducing lateral harmful vibrations of the micropipette tip;

the double-tapered face shaped gasket self-sealing mechanism effectively realizes the functions of air sealing and liquid sealing, and the mechanism has better clamping and stabilizing effect on the micropipette; and the "flexible hinge mechanism-base" ultrasonic energy transfer connection is optimized, that is, the design of flange surface contact and the reinforcing rib greatly reduces the overall quality of the mechanism and improves the energy transfer efficiency of piezoelectric ceramics without impairing the overall strength and function of the micropipette.

BRIEF DESCRIPTION OF THE DRAWINGS

In order to more clearly illustrate the technical solutions in the embodiments of the present invention or the prior art, the drawings used in the description of the embodiments or the prior art will be briefly described below. Obviously, the drawings in the following description are only a few embodiments described in the present invention, and other drawings can be obtained from those skilled in the art without any inventive effort.

DETAILED DESCRIPTION

In order to make those skilled in the art better understand the technical solutions in the present invention, the technical solutions in the embodiments of the present invention will be clearly and completely described in conjunction with the accompanying drawings in the embodiments of the present invention. The embodiments are only a part of the embodiments of the present invention, and not all of the embodiments. All other embodiments obtained by those skilled in the art based on the embodiments of the present invention without creative efforts shall fall within the scope of the present invention.

Referring to FIG. 1, FIG. 2, FIG. 11a, FIG. 11b, FIG. 12 and FIG. 13, a specific embodiment of the present invention discloses a piezoelectric ultrasonic microinjection device based on a flexible hinge mechanism, which mainly includes a micropipette clamping and self-sealing module, a flexible hinge filtering mechanism and an energy transmission mechanism, and specifically includes:

a cover 10, a flexible hinge mechanism 20, a base 30, a screw cap 40 and an end cap 50 fixedly assembled together, the base 30 being provided with a pump interface 35; and a micropipette 60 fixedly mounted in the base, the screw cap and the end cap and extending outward, the micropipette 60 being in communication with the pump interface 35;

wherein the flexible hinge mechanism 20 includes a housing 21, a piezoelectric ceramic package module 22 encapsulated in the housing, a central shaft 23 fixedly mounted to the piezoelectric ceramic package module and the base, and a vibration output shaft 24 extending from the piezoelectric ceramic package module 22 into the central shaft 23, a plurality of flexible hinge beams 25 being disposed between the central shaft 23 and the housing 21.

In this embodiment, the end cap 50 and the screw cap 40 as well as the screw cap 40 and the base 30 are respectively fixedly mounted to each other through a thread.

Figure 1:
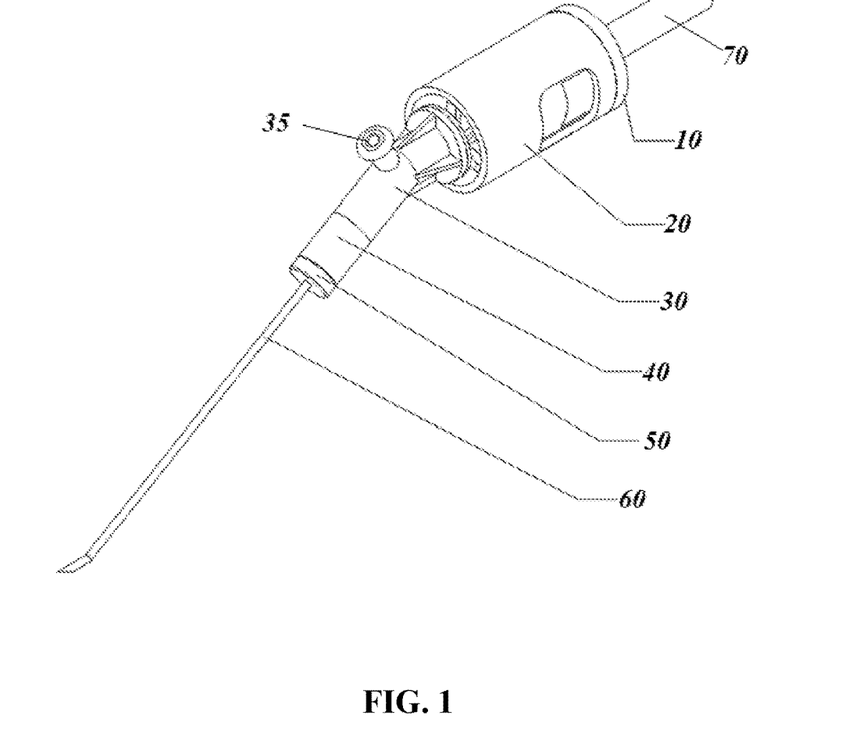
FIG. 1 is a schematic perspective view of a piezoelectric ultrasonic microinjection device according to an embodiment of the present invention.
Figure 2:
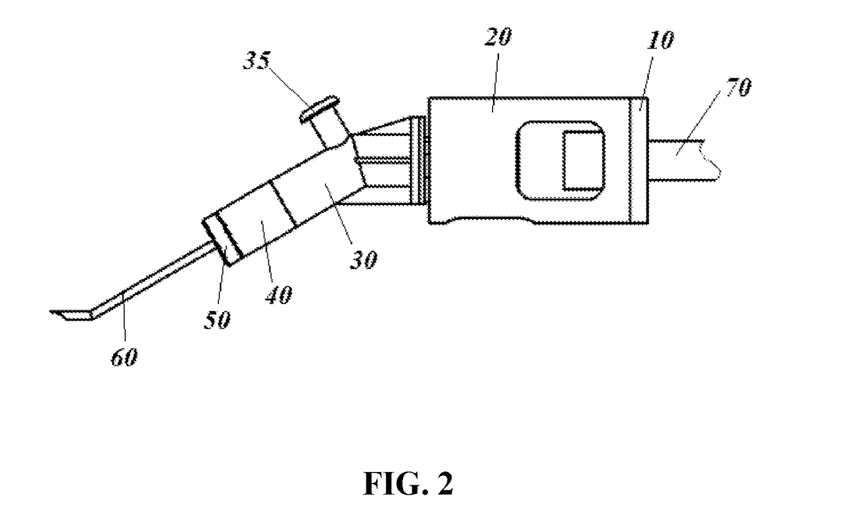
FIG. 2 is a front elevational view of a piezoelectric ultrasonic microinjection device according to an embodiment of the present invention.
Figure 3:
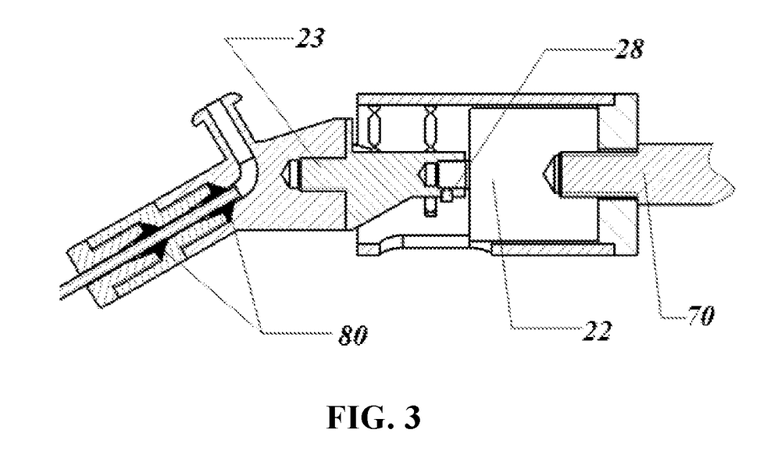
FIG. 3 is a schematic cross-sectional structural view of a piezoelectric ultrasonic microinjection device according to an embodiment of the present invention.
Figure 4:
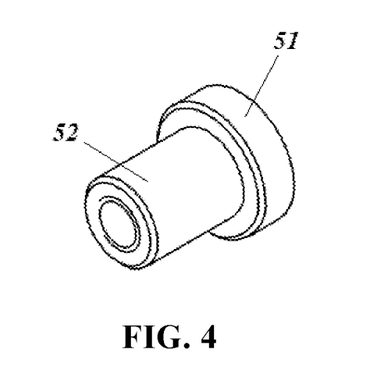
FIG. 4 is a schematic perspective view of an end cap according to an embodiment of the present invention.
Figure 5:
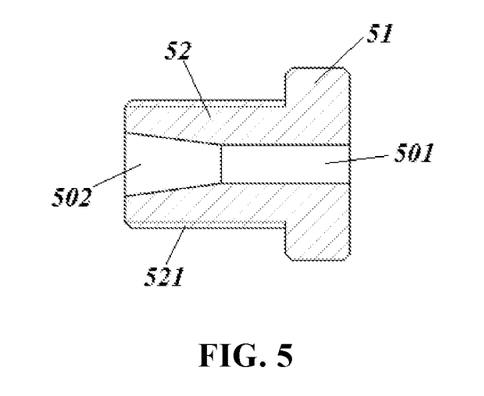
FIG. 5 is a schematic cross-sectional structural view of an end cap according to an embodiment of the present invention.
Figure 6:
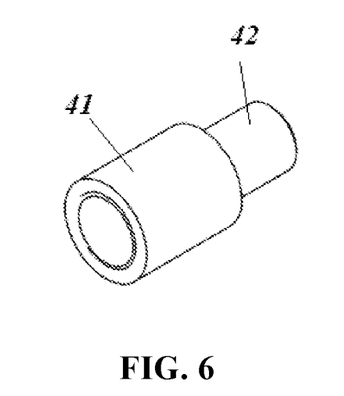
FIG. 6 is a schematic perspective view of a screw cap according to an embodiment of the present invention.

As shown in FIG. 3 to FIG. 5, the end cap 50 includes an end cap body 51 and an end cap mounting portion 52. An outer diameter of the end cap body 51 is greater than that of the end cap mounting portion 52. An outer side of the end cap mounting portion 52 is provided with a first thread 521 fixedly mounted with the screw cap. A first cavity 501 and a second cavity 502 are formed in the end cap 50 in a direction from the end cap body 51 toward the end cap mounting portion 52. The second cavity 502 is tapered.

Specifically, the end cap 50 in the embodiment is a second-order stepped shaft-shaped part, and is provided with an external thread on one side of a small cylindrical surface, a tapered face hole on an end face of the small cylindrical surface, and a fully through glossy face hole at a central axis which passes through the entire part, with an inner diameter of 1.2 mm slightly greater than the outer diameter of the micropipette 60 which is 1 mm for the purpose of facilitating the mounting of the micropipette.

As shown in FIGS. 1-3, 6, and 7, the screw cap 40 includes a screw cap body 41 and a screw cap mounting portion 42. An outer diameter of the screw cap body 41 is greater than that of the screw cap mounting portion 42. An inner side of the screw cap body 41 is provided with a second thread 411 fixedly mounted to the end cap 50. An outer side of the screw cap mounting portion 42 is provided with a third thread 421 fixedly mounted to the base 30. A third cavity 401, a fourth cavity 402, and a fifth cavity 403 are formed in the screw cap 40 in a direction from the screw cap body to the screw cap mounting portion. The fifth cavity 403 is tapered.

Figure 7:
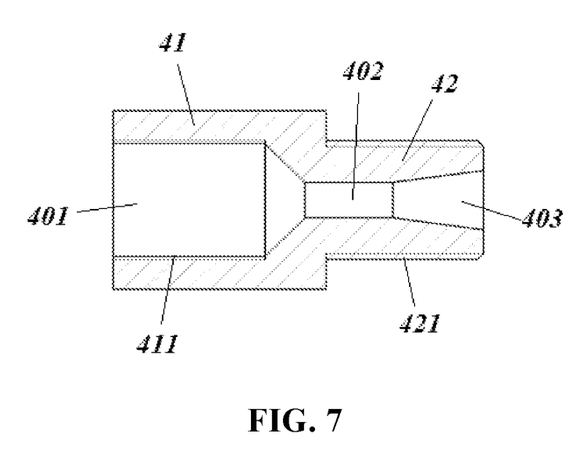
FIG. 7 is a schematic cross-sectional structural view of a screw cap according to an embodiment of the present invention.

Specifically, in this embodiment, the screw cap 40 is matched with the end cap 50. The screw cap 40 is also a second-step stepped shaft-shaped part. A large-diameter end of the screw cap 40 is provided with an internal thread matched with the end cap 50 with a thread length slightly less than that of an external thread of the end cap 50 in order to fully screw the end cap 50 into the internal thread of the screw cap 40. As shown in FIG. 7, an end face of the internal thread of the screw cap 40 is provided with a tapered face hole surface with a large diameter being the outer diameter of the internal thread. An outer cylindrical surface of the other end (small diameter) of the screw cap 40 is provided with an external thread with a size parameter being the same as that of the external thread of the end cap 50. In addition, similar to the design of the end cap 50, the screw cap 40 is provided with a tapered face hole at an end face of the external thread with a size parameter being the same as that of the tapered face hole of the end cap 50. At the same time, for the through mounting of the micropipette 60, a through hole having an inner diameter of 1.2 mm is also formed in the central shaft.

As shown in FIGS. 1-3 and 6-9, the base 30 includes a bent section 31 fixedly mounted to the screw cap 40, and a horizontal section 32 fixedly mounted to the flexible hinge mechanism 20. The bent section 31 and the horizontal section 32 are respectively fixedly mounted to the screw cap and the flexible hinge mechanism through a thread.

Figure 8:
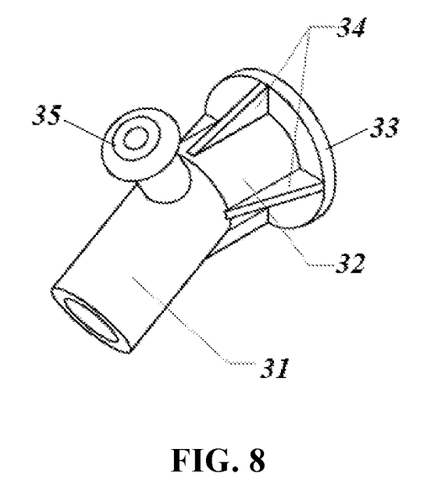
FIG. 8 is a schematic perspective view of a base according to an embodiment of the present invention.
Figure 9:
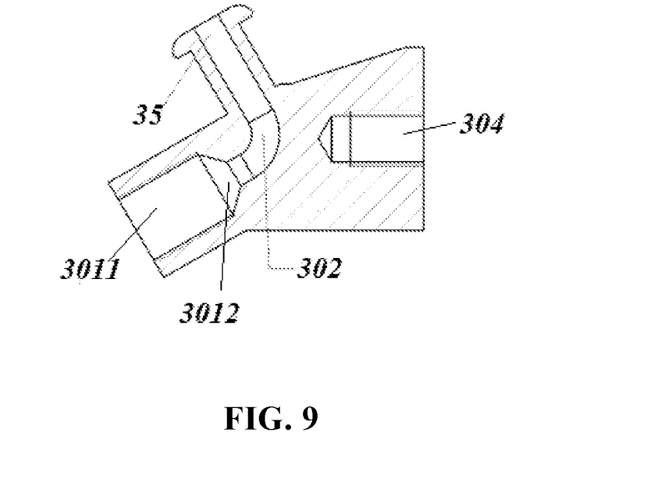
FIG. 9 is a schematic cross-sectional structural view of a base according to an embodiment of the present invention.

A fourth thread (not shown) fixedly mounted to the screw cap is disposed on an inner side of the bent section 31. A sixth cavity 3011 and a seventh cavity 3012 are disposed in the bent section 31. An eighth cavity 304 is disposed in the horizontal section 32. The seventh cavity 3012 is tapered. The sixth cavity 3011 is in communication with the pump interface 35 through the seventh cavity 3012 and a micro flow channel 302.

An inner side of the horizontal section 32 is provided with a fifth thread (not shown). An outer side of an end of the central shaft of the flexible hinge mechanism 20 is provided with a sixth thread. The base 30 and the flexible hinge mechanism 20 are fixedly mounted by the fifth thread and the sixth thread.

In addition, an end of the horizontal section 32 is provided with a first flange 33. A plurality of first reinforcing ribs 34 is disposed between the first flange 33 and the horizontal section 32.

Specifically, the base 30 is divided into two sections, and is divided into a bent section 31 and a horizontal section 32 during mounting. The bent section 31 is provided with an internal thread matched with the external thread of the screw cap 40 with a thread length slightly smaller than that of the external thread of the screw cap 40, in order to completely screw the screw cap 40 into an internal thread of the base 30. Similarly, a tapered face hole is formed at an end face of the internal thread in the base 30 with a size being the same as that of the tapered face hole at the end face of the internal thread of the screw cap 40. In addition, as shown in FIG. 9, a microchannel 302 is provided in the horizontal section 32 extending from the pump interface 35 at the upper end to the end face of the internal thread of the bent section 32. As shown in FIG. 3, an end face of the horizontal section of the base 30 is provided with an internal thread matched with the external thread of the central shaft of the flexible hinge mechanism 20. The flexible hinge mechanism 20 filters and buffers the ultrasonic energy generated by the piezoelectric ceramic package module 22 through the flexible hinge and transmits it to the base 30 through the vibration output shaft 24.

Referring to FIG. 1, FIG. 3, FIG. 10a, and FIG. 10b, a gasket 80 is disposed between the end cap 50 and the screw cap 40 and between the screw cap 40 and the base 30. Two sides of the gasket 80 are different first tapered face 81 and second tapered face 82.

Figure 10A:
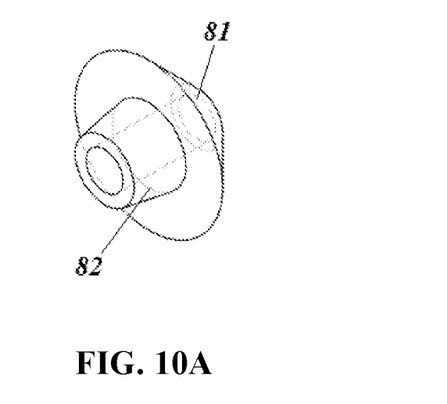
FIG. 10a is a schematic perspective view of a gasket in an embodiment of the present invention.
Figure 10B:
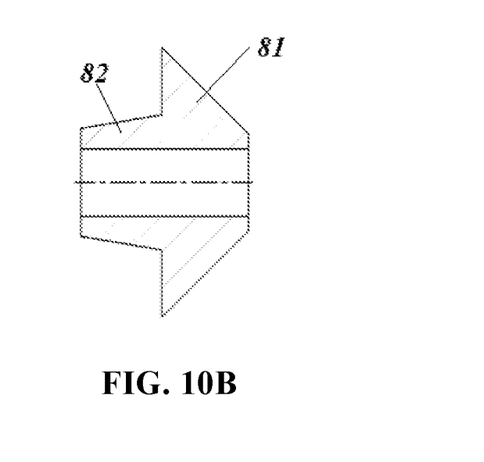
FIG. 10b is a cross-sectional structural view of a gasket in an embodiment of the present invention.

Specifically, two ends of the gasket 80 are both tapered faces which are divided into a first tapered face 81 and a second tapered face 82. The gasket 80 has a through hole at a central axis the size of which is exactly the outer diameter of the micropipette 60. During assembly, the gasket 80 is first mounted into the tapered face hole at the bottom of the internal thread of the base 30, the first tapered face 81 is matched with the tapered face hole of the base 30, and then the screw cap 40 is screwed but not tightened. Similarly, a gasket 80 is placed at the bottom of the internal thread of the screw cap 40, the first tapered face 81 of the gasket 80 is matched therewith, and then the end cap 50 is screwed but not tightened. Finally, the micropipette 60 is adjusted to be properly inserted from the end face hole of the first tapered face 81 of the end cap 50 until the end face of the micropipette 60 is brought to the position of the microchannel 302 of the base 30 to stop. Finally, the screw cap 40 and the end cap 50 are tightened at the same time until they are screwed to the limit position and cannot rotate any more. The second tapered face 82 of the gasket 80 is matched with the tapered face hole at the end face of the external thread of the screw cap 40. The tapered face of the gasket 80 is slightly greater in size than the matched tapered face hole.

The design purpose of the gasket 80 is as follows: in the process of screwing the end cap 50 into the internal threaded hole of the screw cap 40, due to the elastic deformation characteristic of the gasket 80, the first tapered face 81 of the gasket 80 is subjected to a tightening force to press the wall of the tapered face hole at the bottom of the internal thread of the base 30, and at the same time, the gasket 80 is subjected to a reaction force so that the second tapered face 82 of the gasket 80 presses the wall of the tapered face hole at the external thread of the screw cap 40, thereby achieving a self-sealing effect.

In addition, since the tapered face of the gasket 80 is subjected to a tightening force, when mechanically decomposed, due to the stress of the tapered face, a radial force is generated on the surface of the micropipette wall of the micropipette 60, so that the inner cylindrical hole wall of the gasket 80 and the outer cylindrical surface of the micropipette 60 achieves an automatic sealing effect during the tightening process. When the experimenter tightens the screw cap 40, the gasket 80 reaches the limit of elastic deformation, thereby pressing the inner wall, and forming a multi-directional multi-angle self-sealing environment through the surface contact. Similarly, during the process of screwing the end cap 50 into the internal thread of the screw cap 40, the first tapered face 81 of the gasket 80 also presses the wall of the tapered face hole at the bottom of the internal threaded hole in the screw cap 40. At the same time, due to being subjected to a reaction force, the second tapered face 82 of the gasket 80 presses the tapered face hole of the end face of the external thread of the end cap 50, and the inner hole wall of the gasket 80 presses the outer wall of the micropipette 60 to achieve a self-sealing effect.

As shown in FIG. 3, since the micropipette 60 needs to perform micromanipulation under the high frequency vibration of the piezoelectric ceramic package module 22 when rupturing the cell, the two-point supporting design of the micropipette 60 for clamping can effectively avoid the radial vibration of the micropipette 60, and can transmit the axial vibration transmitted by the vibration output shaft 24 of the flexible hinge mechanism more efficiently. In addition, since the gasket 80 and the micropipette 60 are in surface contact herein, compared with the conventional point contact and hard contact, the design of the gasket 80 can better fix and clamp the micropipette 60 and prevent the micropipette 60 and the clamping mechanism from relative displacement, thereby reducing the mechanical wear between the micropipette 60 and the clamping screw cap 40, the base 30 and the end cap 50. Therefore, the design of the gasket 80 being matched with the corresponding base 30, the screw cap 40, and the tapered face hole of the end cap 50 not only can achieve a better sealing effect, but also has a more stable and firm clamping and fixing of the micropipette 60. Problems such as "radial rotation" and "axial slip" of the micropipette 60 will not occur during use.

Referring to FIG. 3, FIG. 8, FIG. 11*a*, FIG. 11*b*, and FIG. 12, a first flange 33 is disposed on the end face of the horizontal section 32 of the base 30. A second flange 26 is disposed on the central shaft 23 of the flexible hinge mechanism 20. The first flange 33 and the second flange 26 are correspondingly disposed. The second flange 26 is provided with a threaded hole at the end face thereof which is exactly the same as the outer circle diameter of the end face of the central shaft 23 of the flexible hinge mechanism and matched with the external thread section of the central shaft 23 of the flexible hinge structure. During the actual assembly process, the central shaft 23 of the flexible hinge mechanism is completely screwed into the internal threaded hole of the end face of the first flange 33 of the base 30 until the end face of the central shaft 23 of the flexible hinge mechanism 20 is matched with the end face of first flange 33 of the horizontal section of the base 30 to achieve surface contact.

As shown in FIG. 8, a first rib is sequentially disposed in the "3 o'clock", "6 o'clock", "9 o'clock", and "12 o'clock" directions between the first flange 33 and the outer cylinder of the horizontal section of the base 30. The purpose is to enhance the structural strength of the base 30 when the vibration output shaft 24 of the flexible hinge mechanism 20 transmits the high frequency vibration to the base 30 through the central shaft 23, and at the same time, to reduce its own weight and improve the energy transfer efficiency.

As shown in FIG. 3, FIG. 11*a*, FIG. 11*b* and FIG. 12, the flexible hinge mechanism 20 is a single piece. The housing 21 is a cylindrical housing. The central shaft 23 and the inner wall of the housing 21 are connected by a flexible hinge beam 25. The flexible hinge beam 25 is a "V" type flexible hinge beam provided with a plurality of V-shaped recesses. The flexible hinge beam is distributed in a circumferential array with an equal angle of 120° at positions of 0°, 120°, 240° in the end face direction centered on the central shaft 23, and the flexible beams in each direction are distributed in a parallel linear array of equidistant double flexible hinge beams at a certain distance in the axial direction. Therefore, a total of six flexible hinge beams 25 are connected to the housing 21 on the center shaft 23.

Figure 11A:
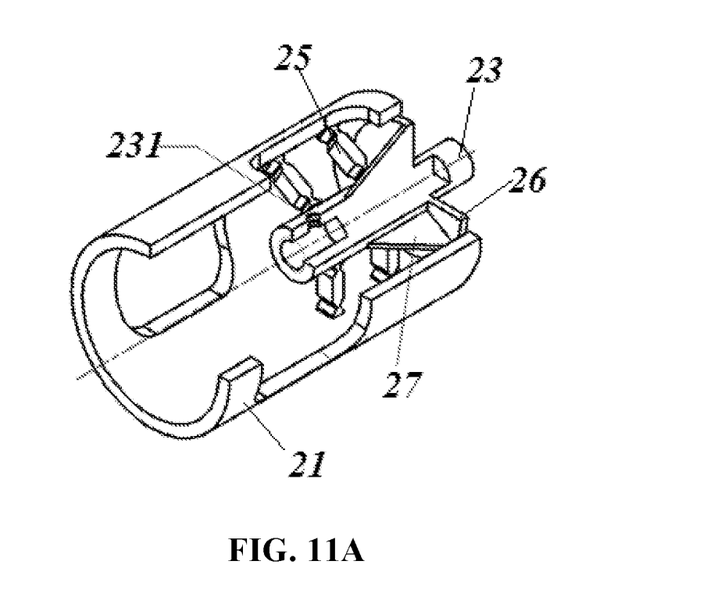
FIG. 11a is a schematic perspective view of a flexible hinge mechanism according to an embodiment of the present invention.
Figure 11B:
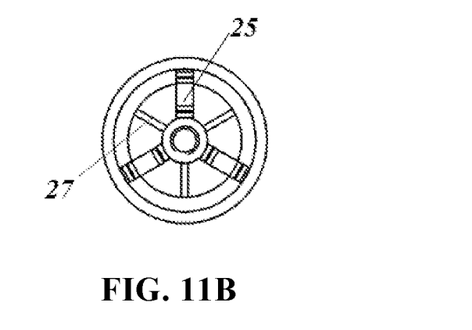
FIG. 11b is a front elevational view of a flexible hinge mechanism according to an embodiment of the present invention.
Figure 12:
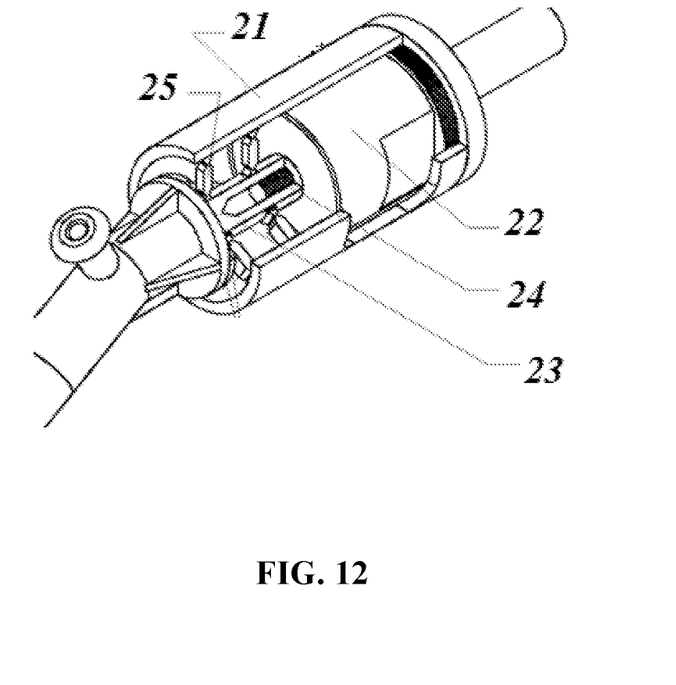
FIG. 12 is a schematic view of an assembly structure of a flexible hinge mechanism according to an embodiment of the present invention.

Through theoretical calculation and finite element analysis, the "V" type flexible hinge beam design has the best axial vibration transmission efficiency, and the filtering effect on the radial residual vibration is also the best. A threaded hole is provided at the end face of the center shaft 23 to be matched with the external thread of the vibration output shaft 24 of the piezoelectric ceramic package module 22. In addition, in order to strengthen the strength between the central shaft 23 and the vibration output shaft 24 of the piezoelectric ceramic package module, and to ensure the transmission efficiency of the ultrasonic vibration energy, a plurality of second reinforcing ribs 27 is provided between the second flange 26 and the center shaft 23 which is in the middle of three flexible hinge beams 25, and is also distributed in an array of 120° centered on the axis. In the process of transmitting the ultrasonic vibration into the central shaft 23 of the flexible hinge mechanism 20 by the piezoelectric ceramic package module 22 through the vibration output shaft 24, in order to avoid loosening of the screw connection between the two under high frequency vibration, the cylindrical surface of the central shaft 23 of the flexible hinge mechanism 20 is provided with a threaded through hole. When the threaded section of the vibration output shaft 24 of the piezoelectric ceramic package module 22 is completely screwed into the threaded hole of the end face of the flexible hinge mechanism center shaft 23, the connection between the central shaft 23 and the vibration output shaft 24 is strengthened and prevented from loosening by screwing a set screw 28.

Figure 13:
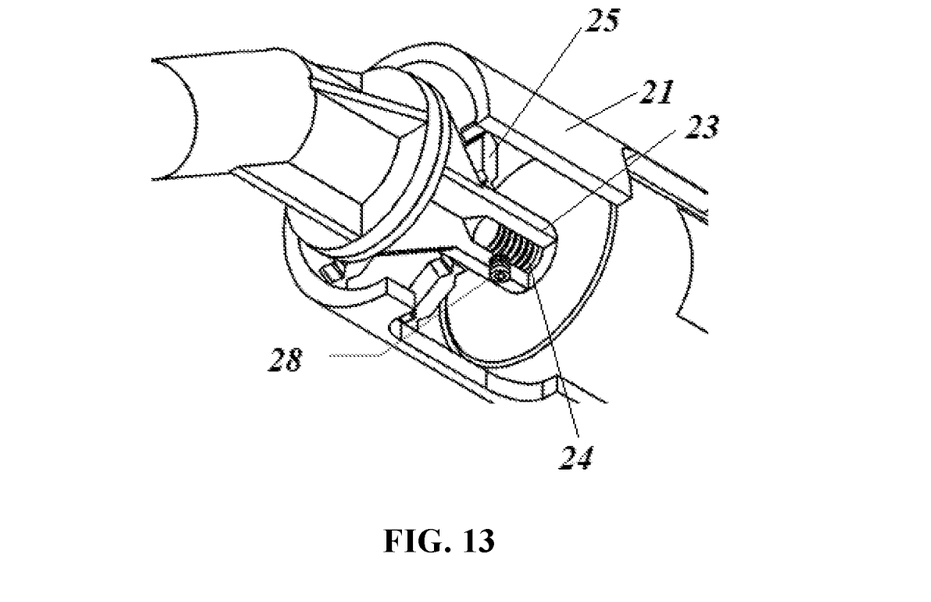
FIG. 13 is another schematic view of an assembly structure of a flexible hinge mechanism according to an embodiment of the present invention.

As shown in FIG. 3, FIG. 12 and FIG. 13, the cover 10 is a second-order stepped shaft part. An external thread (not shown) is provided at a small diameter section of the cover 10. A glossy face through hole is provided at a large-diameter end face of the cover 10. The extremity of the inner wall of the end of the flexible hinge mechanism 20 is provided with an internal thread at a corresponding position which is matched with the external thread at the small shaft end of the cover 10. A fixing rod 70 is also a second-order stepped shaft part, which is provided with an external thread at the cylindrical surface of the small-shaft diameter section of the end face.

The assembly process of the flexible hinge mechanism 20, the piezoelectric ceramic package module 22, the cover 10, the fixing rod 70, and the set screw 28 is as follows: firstly the vibration output shaft 24 of the piezoelectric ceramic package module 22 is screwed into the threaded hole at the end face of the central shaft 23 of the flexible hinge mechanism 20, the set screw 28 is then screwed into a mounting hole 231 on the cylindrical surface of the central shaft 23, so that the head of the set screw 28 abuts against the external thread surface of the vibration output shaft 24, thereby relaxing and reinforcing. The external thread of the small shaft end of the cover 10 is then matched with the internal thread at the end face of the flexible hinge mechanism 20. Next, the small shaft end of the fixing rod 70 is inserted into the glossy face through hole of the large shaft end face of the cover 10, and the external thread of the small shaft end of the fixing rod 70 is screwed into the internal thread at the end face of the tail of the piezoelectric ceramic package module 22. Finally, by continuously tightening the fixing rod 70, the end face of the tail of the piezoelectric ceramic package module 22 and the end face of the small diameter section of the cover 10 are continuously fitted and tightened, and the piezoelectric ceramic package module 22 is also driven to rotate, so that the vibration output shaft 24 of the piezoelectric ceramic package module 22 is continuously tightened and fixed with the threaded hole of the central shaft 23 of the flexible hinge mechanism 20, and the end face of the stepped shaft of the fixing rod 70 and the end face of the large shaft diameter section of the cover 10 are tightly fitted, thereby realizing the assembly and fastening process of the piezoelectric ceramic package module 22, the fixing rod. 70, the cover 10 and the flexible hinge mechanism housing 21.

The working principle of the piezoelectric ultrasonic microinjection device based on a flexible hinge mechanism in the present invention is as follows:

The fixed rod 70 is fixed to the frame and remains absolutely stationary relative to the static ground. The end face thread of the head of the fixing rod 70 is screwed through the through hole of the cover 10 into the threaded hole of the end face of the piezoelectric ceramic package module 22, and the cover 10, the piezoelectric ceramic package module 22 and the fixing rod 70 are fixed by screwing. Moreover, the flexible hinge mechanism housing 21 is also fixed to the cover 10 by a screw connection, so the flexible hinge mechanism housing 21, the cover 10, the fixing rod 70, and the piezoelectric ceramic package module 22 are all fixed ends. After the piezoelectric ceramic package module 22 is connected to a power source, the vibration output shaft 24 generates high-frequency vibration, and the vibration is transmitted into the central shaft 23 of the flexible hinge mechanism 20 through the screw connection between the vibration output shaft 24 and the center shaft 23. Since the piezoelectric ceramic package module 22 generates a small amount of irregular radial vibration during actual motion, if the energy is directly transmitted to the base 30 without any filtering and buffering, the radial residual vibration will be amplified to a large lateral vibration of the micropipette tip of the micropipette 60 after being transported over a long distance to the micropipette tip, which is conducive to cell microinjection and membrane rupture. In the V-shaped flexible hinge beam, the central shaft can only be displaced along the axial direction due to the restraining action of the three-way flexible hinge, and any radial residual vibration will be absorbed by the three-way flexible hinge beam. Therefore, the central shaft, the ribs, the flanges and the output shaft of the flexible hinge mechanism are integral, all of which are movable ends, and the whole is linearly high-frequency reciprocating with respect to the fixed end section (stationary reference). The central shaft finally transmits the filtered ultrasonic vibration energy to the vibration output shaft, and finally transmits the vibration energy to the base through the screw connection of the vibration output shaft and the base.

It can be seen from the above technical solutions that the present invention has the following beneficial effects:

aiming at the harmful radial vibration transmitted by the piezoelectric ceramic package module to the micropipette tip, a three-dimensional flexible hinge mechanism is designed for the piezoelectric ceramic package module, which can effectively filter and buffer the radial harmful vibration of the vibration output shaft while maintaining a high energy transmission efficiency, thereby reducing lateral harmful vibrations of the micropipette tip;

the double-tapered face shaped gasket self-sealing mechanism effectively realizes the functions of air sealing and liquid sealing, and the mechanism has better clamping and stabilizing effect on the micropipette; and the "flexible hinge mechanism-base" ultrasonic energy transfer connection is optimized, that is, the design of flange surface contact and the reinforcing rib greatly reduces the overall quality of the mechanism and improves the energy transfer efficiency of piezoelectric ceramics without impairing the overall strength and function of the micropipette.

Therefore, the present invention can meet bioengineering micromanipulation experiments of different needs, such as: nuclear transfer, single sperm injection, transgenic injection, and the like. At the same time, because the micropipette clamping section adopts a reinforcing rib design, the overall quality of the micropipette is greatly reduced, and the three-dimensional flexible hinge mechanism is adopted to effectively reduce the radial vibration of the micropipette tip caused by the piezoelectric ceramic, thereby effectively alleviating the mechanical damage caused by injection to the cells and improve the success rate of the experiment. At the same time, the present invention has the advantages of simple structure, good interchangeability of components, easy assembly, and relatively low processing cost, which simplifies the experimental cost and complexity of the microinjection experiment operation.

It is apparent to those skilled in the art that the present invention is not limited to the details of the above-described exemplary embodiments, and the present invention can be embodied in other specific forms without departing from the spirit or essential characteristics of the present invention. Therefore, the present embodiments are to be considered as illustrative and not restrictive, and the scope of the present invention is defined by the appended claims instead of the above description. All changes falling within the meaning and scope of equivalent elements of the claims are included in the present invention. Any reference signs in the claims should not be construed as limiting the claim.

In addition, it should be understood that although the description is described in terms of embodiments, not every embodiment includes only one independent technical solution. The narration of the specification is merely for the sake of clarity, and those skilled in the art should regard the specification as a whole. The technical solutions in the respective embodiments may also be combined as appropriate to form other embodiments that can be understood by those skilled in the art.

The invention claimed is:

1. A piezoelectric ultrasonic microinjection device based on a flexible hinge mechanism, the device comprising:
   a cover, a flexible hinge mechanism, a base, a screw cap and an end cap fixedly assembled together, the base being provided with a pump interface; and
   a micropipette fixedly mounted in the base, the screw cap and the end cap and extending outward, the micropipette being in communication with the pump interface;
   wherein the flexible hinge mechanism comprises a housing, a piezoelectric ceramic package module encapsulated in the housing, a central shaft fixedly mounted with the piezoelectric ceramic package module and the base, and a vibration output shaft extending from the piezoelectric ceramic package module into the central shaft, a plurality of flexible hinge beams being disposed between the central shaft and the housing;

wherein the end cap and the screw cap as well as the screw cap and the base are respectively fixedly mounted to each other through a thread;

wherein the base comprises a bent section fixedly mounted to the screw cap, and a horizontal section fixedly mounted with the flexible hinge mechanism, the bent section and the horizontal section being respectively fixedly mounted to the screw cap and the flexible hinge mechanism through a thread;

wherein an end of the horizontal section is provided with a first flange, and a plurality of first reinforcing ribs is provided between the first flange and the horizontal section; and wherein the central shaft of the flexible hinge mechanism is provided with a second flange, and a plurality of second reinforcing ribs is provided between the second flange and the central shaft.

2. The piezoelectric ultrasonic microinjection device based on a flexible hinge mechanism according to claim 1, wherein a gasket is disposed between the end cap and the screw cap and/or between the screw cap and the base, and two sides of the gasket are different first and second tapered faces.

3. The piezoelectric ultrasonic microinjection device based on a flexible hinge mechanism according to claim 1, wherein the end cap comprises an end cap body and an end cap mounting portion, an outer diameter of the end cap body being greater than that of the end cap mounting portion, and an outer side of the end cap mounting portion being provided with a first thread, the first thread being adapted for fixedly mounting the end cap mounting portion to the screw cap.

4. The piezoelectric ultrasonic microinjection device based on a flexible hinge mechanism according to claim 3, wherein a first cavity and a second cavity are formed in the end cap in a direction from the end cap body toward the end cap mounting portion, the second cavity being tapered.

5. The piezoelectric ultrasonic microinjection device based on a flexible hinge mechanism according to claim 2, wherein the screw cap comprises a screw cap body and a screw cap mounting portion, an outer diameter of the screw cap body being greater than that of the screw cap mounting portion, an inner side of the screw cap body being provided with a second thread fixedly mounted to the end cap, and an outer side of the screw cap mounting portion being provided with a third thread fixedly mounted to the base.

6. The piezoelectric ultrasonic microinjection device based on a flexible hinge mechanism according to claim 5, wherein a third cavity, a fourth cavity and a fifth cavity are formed in the screw cap in a direction from the screw cap body to the screw cap mounting portion, the fifth cavity being tapered.

7. The piezoelectric ultrasonic microinjection device based on a flexible hinge mechanism according to claim 1, wherein an inner side of the bent section is provided with a fourth thread fixedly mounted to the screw cap.

8. The piezoelectric ultrasonic microinjection device based on a flexible hinge mechanism according to claim 1, wherein a sixth cavity and a seventh cavity are provided in the bent section, and an eighth cavity is provided in the horizontal section, the seventh cavity being tapered, and the sixth cavity being in communication with the pump interface through the seventh cavity and a micro flow channel.

9. The piezoelectric ultrasonic microinjection device based on a flexible hinge mechanism according to claim 1, wherein an inner side of the horizontal section is provided with a fifth thread, an outer side of an end of the central shaft of the flexible hinge mechanism is provided with a sixth thread, and the base and the flexible hinge mechanism are fixedly mounted through the fifth thread and the sixth thread.

10. The piezoelectric ultrasonic microinjection device based on a flexible hinge mechanism according to claim 1, wherein the flexible hinge beams are provided with a plurality of V-shaped recesses.

11. The piezoelectric ultrasonic microinjection device based on a flexible hinge mechanism according to claim 1, wherein the flexible hinge beams are distributed in a circumferential array with an equal angle of 120° centered on the central shaft, and the flexible hinge beams in each direction are distributed in a parallel linear array of equidistant double flexible hinge beams at a certain distance in the axial direction.

12. The piezoelectric ultrasonic microinjection device based on a flexible hinge mechanism according to claim 1, wherein the central shaft is provided with a mounting hole, and a screw is fixedly mounted in the mounting hole to fix the central shaft and the vibration output shaft.

* * * * *